(12) United States Patent
Tanner, Jr. et al.

(10) Patent No.: US 10,417,379 B2
(45) Date of Patent: Sep. 17, 2019

(54) HEALTH LENDING SYSTEM AND METHOD USING PROBABILISTIC GRAPH MODELS

(71) Applicant: Change Healthcare Holdings, LLC, Nashville, TN (US)

(72) Inventors: Theodore C. Tanner, Jr., San Mateo, CA (US); Colin Erik Alstad, San Mateo, CA (US)

(73) Assignee: CHANGE HEALTHCARE HOLDINGS, LLC, Nashville, TN (US)

( * ) Notice: Subject to any disclaimer, the term of this patent is extended or adjusted under 35 U.S.C. 154(b) by 0 days.

(21) Appl. No.: 15/001,703

(22) Filed: Jan. 20, 2016

(65) Prior Publication Data

US 2016/0210423 A1 Jul. 21, 2016

Related U.S. Application Data

(60) Provisional application No. 62/105,503, filed on Jan. 20, 2015.

(51) Int. Cl.
| | |
|---|---|
| *G06F 19/00* | (2018.01) |
| *G06N 7/00* | (2006.01) |
| *G06Q 40/02* | (2012.01) |
| *G16H 40/20* | (2018.01) |
| *G16H 50/30* | (2018.01) |

(52) U.S. Cl.
CPC ........... *G06F 19/328* (2013.01); *G06N 7/005* (2013.01); *G06Q 40/025* (2013.01); *G16H 40/20* (2018.01); *G16H 50/30* (2018.01)

(58) Field of Classification Search
None
See application file for complete search history.

(56) References Cited

U.S. PATENT DOCUMENTS

| | | | |
|---|---|---|---|
| 5,872,021 | A | 2/1999 | Matsumoto et al. |
| 6,546,428 | B2 | 4/2003 | Baber et al. |
| 7,386,565 | B1 | 6/2008 | Singh et al. |
| 7,917,378 | B2 | 3/2011 | Fitzgerald et al. |
| 7,917,515 | B1 | 3/2011 | Lemoine |
| 7,970,802 | B2 | 6/2011 | Ishizaki |
| 7,992,153 | B2 | 8/2011 | Ban |
| 8,073,801 | B1 | 12/2011 | Von Halle et al. |
| 8,095,975 | B2 | 1/2012 | Boss et al. |

(Continued)

FOREIGN PATENT DOCUMENTS

| | | |
|---|---|---|
| GB | 2478440 | 10/2013 |
| WO | WO2012/122065 | 9/2012 |

OTHER PUBLICATIONS

Lin et al., *A simplicial complex, a hypergraph, structure in the latent semantic space of document clustering*, © Elsevier, 2005 (26 pgs.).

(Continued)

*Primary Examiner* — Michael Tomaszewski
(74) *Attorney, Agent, or Firm* — Meunier Carlin & Curfman LLC

(57) ABSTRACT

A system and method for health lending using a probabilistic graph model are described. The system and method may generate a health credit score ("HICO"). The HICO is a score that is a risk measure placed on all entities of a healthcare transaction in which a company that owns or operates the system may have an interest or a company that utilizes the HICO score for its risk assessment.

24 Claims, 15 Drawing Sheets

(56) References Cited

U.S. PATENT DOCUMENTS

| | | |
|---|---|---|
| 8,103,667 B2 | 1/2012 | Azar et al. |
| 8,103,952 B2 | 1/2012 | Hopp |
| 8,203,562 B1 | 6/2012 | Alben et al. |
| 8,229,808 B1 | 7/2012 | Heit |
| 8,286,191 B2 | 10/2012 | Amini et al. |
| 8,359,298 B2 | 1/2013 | Schacher et al. |
| 8,364,501 B2 | 1/2013 | Rana et al. |
| 8,417,755 B1 | 4/2013 | Zimmer |
| 8,495,108 B2 | 7/2013 | Nagpal et al. |
| 8,515,777 B1 | 8/2013 | Rajasenan |
| 8,817,665 B2 | 8/2014 | Thubert et al. |
| 8,984,464 B1 | 3/2015 | Mihal et al. |
| 9,165,045 B2 | 10/2015 | Mok et al. |
| 9,208,284 B1 | 12/2015 | Douglass |
| 2002/0022973 A1 | 2/2002 | Sun et al. |
| 2002/0038233 A1 | 3/2002 | Shubov et al. |
| 2002/0165738 A1 | 11/2002 | Dang |
| 2003/0055668 A1 | 3/2003 | Saran et al. |
| 2003/0097359 A1 | 5/2003 | Ruediger |
| 2003/0171953 A1 | 9/2003 | Narayanan et al. |
| 2003/0217159 A1 | 11/2003 | Schramm-Apple et al. |
| 2003/0233252 A1 | 12/2003 | Haskell et al. |
| 2004/0143446 A1 | 7/2004 | Lawrence |
| 2005/0010452 A1 | 1/2005 | Lusen |
| 2005/0071189 A1 | 3/2005 | Blake et al. |
| 2005/0102170 A1 | 5/2005 | Lefever et al. |
| 2005/0137912 A1 | 6/2005 | Rao et al. |
| 2005/0152520 A1 | 7/2005 | Logue |
| 2005/0182780 A1 | 8/2005 | Forman et al. |
| 2005/0222912 A1 | 10/2005 | Chambers |
| 2006/0036478 A1 | 2/2006 | Aleynikov et al. |
| 2006/0074290 A1 | 4/2006 | Chen et al. |
| 2006/0089862 A1 | 4/2006 | Anandarao et al. |
| 2006/0129428 A1 | 6/2006 | Wennberg |
| 2006/0136264 A1 | 6/2006 | Eaton et al. |
| 2007/0113172 A1 | 5/2007 | Behrens et al. |
| 2007/0118399 A1 | 5/2007 | Avinash et al. |
| 2007/0156455 A1 | 7/2007 | Tarino et al. |
| 2007/0174101 A1 | 7/2007 | Li et al. |
| 2007/0180451 A1 | 8/2007 | Ryan et al. |
| 2007/0214133 A1 | 9/2007 | Liberty et al. |
| 2007/0233603 A1 | 10/2007 | Schmidgall et al. |
| 2007/0260492 A1 | 11/2007 | Feied et al. |
| 2007/0276858 A1 | 11/2007 | Cushman et al. |
| 2007/0288262 A1 | 12/2007 | Sakaue |
| 2008/0013808 A1 | 1/2008 | Russo et al. |
| 2008/0082980 A1 | 4/2008 | Nessland et al. |
| 2008/0091592 A1* | 4/2008 | Blackburn ........... G06Q 40/025 705/38 |
| 2008/0126264 A1 | 5/2008 | Tellefsen et al. |
| 2008/0133436 A1* | 6/2008 | Di Profio ............. G06N 7/005 706/12 |
| 2008/0288292 A1 | 11/2008 | Bi et al. |
| 2008/0295094 A1 | 11/2008 | Korupolu et al. |
| 2008/0319983 A1 | 12/2008 | Meadows |
| 2009/0083664 A1 | 3/2009 | Bay |
| 2009/0125796 A1 | 5/2009 | Day et al. |
| 2009/0192864 A1 | 7/2009 | Song et al. |
| 2009/0198520 A1 | 8/2009 | Piovanetti-Perez |
| 2009/0300054 A1 | 12/2009 | Fisher et al. |
| 2009/0307104 A1 | 12/2009 | Weng |
| 2009/0313045 A1 | 12/2009 | Boyce |
| 2010/0076950 A1 | 3/2010 | Kenedy et al. |
| 2010/0082620 A1 | 4/2010 | Jennings, III et al. |
| 2010/0088108 A1 | 4/2010 | Machado |
| 2010/0088119 A1 | 4/2010 | Tipirneni |
| 2010/0138243 A1 | 6/2010 | Carroll |
| 2010/0217973 A1 | 8/2010 | Kress et al. |
| 2010/0228721 A1 | 9/2010 | Mok et al. |
| 2010/0295674 A1 | 11/2010 | Hsieh et al. |
| 2010/0332273 A1 | 12/2010 | Balasubramanian et al. |
| 2011/0015947 A1 | 1/2011 | Erry et al. |
| 2011/0055252 A1 | 3/2011 | Kapochunas et al. |
| 2011/0071857 A1 | 3/2011 | Malov et al. |
| 2011/0137672 A1* | 6/2011 | Adams ................ G06Q 10/06 705/2 |
| 2011/0218827 A1 | 9/2011 | Kennefick et al. |
| 2011/0270625 A1 | 11/2011 | Pederson et al. |
| 2012/0011029 A1 | 1/2012 | Thomas et al. |
| 2012/0035984 A1 | 2/2012 | Srinivasa et al. |
| 2012/0078940 A1 | 3/2012 | Kolluri et al. |
| 2012/0130736 A1 | 5/2012 | Dunston et al. |
| 2012/0158429 A1 | 6/2012 | Murawski et al. |
| 2012/0158750 A1 | 6/2012 | Faulkner et al. |
| 2012/0173279 A1 | 7/2012 | Nessa et al. |
| 2012/0245958 A1 | 9/2012 | Lawrence et al. |
| 2012/0246727 A1 | 9/2012 | Elovici et al. |
| 2012/0290320 A1 | 11/2012 | Kurgan et al. |
| 2012/0290564 A1 | 11/2012 | Mok et al. |
| 2013/0030827 A1 | 1/2013 | Snyder et al. |
| 2013/0044749 A1 | 2/2013 | Eisner et al. |
| 2013/0085769 A1 | 4/2013 | Jost et al. |
| 2013/0138554 A1* | 5/2013 | Nikankin ............. G06Q 40/02 705/38 |
| 2013/0166552 A1 | 6/2013 | Rozenwald et al. |
| 2013/0204940 A1 | 8/2013 | Kinsel et al. |
| 2013/0304903 A1 | 11/2013 | Mick et al. |
| 2014/0046931 A1 | 2/2014 | Mok et al. |
| 2014/0056243 A1 | 2/2014 | Pelletier et al. |
| 2014/0059084 A1 | 2/2014 | Adams et al. |
| 2014/0088981 A1 | 3/2014 | Momita |
| 2014/0136233 A1 | 5/2014 | Atkinson et al. |
| 2014/0222482 A1 | 8/2014 | Gautam et al. |
| 2014/0244300 A1 | 8/2014 | Bess et al. |
| 2014/0278491 A1 | 9/2014 | Weiss |
| 2014/0358578 A1 | 12/2014 | Ptachcinski |
| 2014/0358845 A1 | 12/2014 | Mundlapudi et al. |
| 2015/0095056 A1 | 4/2015 | Ryan et al. |
| 2015/0112696 A1 | 4/2015 | Kharraz Tavakol |
| 2015/0142464 A1 | 5/2015 | Rusin et al. |
| 2015/0199482 A1 | 7/2015 | Corbin et al. |
| 2015/0332283 A1 | 11/2015 | Witchey |
| 2016/0028552 A1 | 1/2016 | Spanos et al. |
| 2016/0055205 A1 | 2/2016 | Jonathan et al. |
| 2016/0253679 A1 | 9/2016 | Venkatraman et al. |
| 2016/0328641 A1 | 11/2016 | Alsaud et al. |
| 2017/0091397 A1 | 3/2017 | Shah et al. |
| 2017/0132621 A1 | 5/2017 | Miller et al. |
| 2017/0351821 A1 | 12/2017 | Tanner et al. |
| 2017/0372300 A1 | 12/2017 | Dunlevy et al. |

OTHER PUBLICATIONS

PCT/US16/14117, International Search Report dated Mar. 31, 2016 (2 pgs.).

PCT/US16/14117, Written Opinion dated Mar. 31, 2016 (6 pgs.).

Ahlswede et al., *Network Information Flow*, IEEE Transactions on Information Theory, vol. 46, No. 4; Jul. 2000 (13 pgs.).

Bhattacharya, Indrajit and Getoor, Lise, *Entity Resolution in Graphs*, Department of Computer Science, University of Maryland (2005) (21 pgs.).

Chen et al., *Adaptive Graphical Approach to Entity Resolution*, Jun. 18-23, 2007, Proceedings of the 7th ACM/IEEE-CS Joint Conference on Digital Libraries, pp. 204-213 (10 pgs.).

Christen, *Data Matching, Concepts and Techniques for Record Linkage, Entity Resolution, and Duplicate Detection*, © Springer-Verlag Berlin Heidelberg, 2012 (279 pgs.).

Cohen et al., *A Comparison of String Metrics for Matching Names and Records*, © 2003, American Association for Artificial Intelligence (www.aaai.org) (6 pgs.).

Coleman et al., *Medical Innovation—a diffusion study*; The Bobbs-Merrill Company, Inc., 1966 (248 pgs.).

Domingos et al., *Mining High-Speed Data Streams*, (2000) (10 pgs.).

Greenhalgh et al., *Diffusion of Innovations in Health Service Organisations—a systematic literature review*, Blackwell Publishing, 2005 (325 pgs.).

Jackson et al., *The Evolution of Social and Economic Networks*, Journal of Economic Theory 106, pp. 265-295, 2002 (31 pgs.).

(56) References Cited

OTHER PUBLICATIONS

Jackson, Matthew O., *Social and Economic Networks*, Princeton University Press, 2008 (509 pgs.).
Krempl et al., *Open Challenges for Data Stream Mining Research*, SIGKDD Explorations, vol. 16, Issue 1, Jun. 2014 (64 pgs.).
Rebuge, *Business Process Analysis in Healthcare Environments*, 2011, Ellsevier Ltd., pp. 99-116 (18 pgs.).
Wasserman et al., *Social Network Analysis: Methods and Applications*, Cambridge University Press; 1994 (434 pgs.).
White et al., *Algorithms for Estimating Relative Importance in Networks*, Proceedings of the Ninth ACM SIGKDD International Conference on Knowledge Discovery and Data Mining, 2003 (10 pgs.).
(MATHJAX), *Naive Bayes Categorisation (with some help from Elasticsearch)*, blog post dated Dec. 29, 2013 (https://blog.wtf.sg/2013/12/29/naive-bayes-categorisation-with-some-help-from-elasticsearch/). (8 pgs.).
Webpage: New Health Care Electronic Transactions Standards Versions 5010, D.0, and 3.0, Jan. 2010 ICN 903192; http://www.cms.gov/Regulations-and-Guidance/HIPAA-Adminstrative-Simplification/Versions5010andD0/downloads/w5010BasicsFctCht.pdf (4 pgs.).
Webpage: U.S. Dept. of Health and Human Services, Guidance Regarding Methods for De-identification of Protected Health Information in Accordance with the Health Insurance Portability and Accountability Act (HIPAA) Privacy Rule, http://www.hhs.gov/ocr/privacy/hipaa/understanding/coveredentities/De-identification/guidance.html printed Oct. 15, 2015 (14 pgs.).
Anonymous: "Oauth—Wikipedia", Sep. 23, 2013. Retrieved from the Internet URL:https://en.wikipedia.org/w/index.php?title+oAuth&oldid+574187532.
Anonymous: "Oauth" Wikipedia—Retrieved from the Internet URL:https://en.wikipedia.org/wiki/Oauth (8 pgs.).
Version 5010 and D.O, Center for Medicare & Medicaid Services (2 pgs).

* cited by examiner

```
example_input_data = {
  'provider_npi': '1033176631',
  'payer': 'medicare',
  'procedrue_cpt_code': '99203',
  'procedures_performed_by_specialty_count': 11412
  'procedures_performed_by_provider': 123,
  'reimburesed_price_stats_for_provider_payer_cpt_code': {'mean': 71.04,
                                                          'std': 25.91},
  'reimburesed_price': 77.50}
```

Provider/Payer Code Example
pdhico.calculate_provider_payer_risk(**example_input_data) = 0.30

FIGURE 9

PDHICO Score = (1 - P(loss) * 100)

PDHICO Score = ((1 − 0.7) * 100) = 30

| PDHICO Score Range | PDHICO Score Category |
|---|---|
| 94-100 | A |
| 90-93 | A- |
| 87-89 | B+ |
| 83-86 | B |
| 80-82 | B- |
| 77-79 | C+ |
| 73-76 | C |
| 70-72 | C- |
| 67-69 | D+ |
| 63-66 | D |
| 60-63 | D- |
| < 60 | F |

PDHCO Example Category = 'F'

FIGURE 11

Example_consumer_data = {
    'consumer_age': 41,
    'consumer_gender': 'male',
    'zipcode': '29412',
    'smoker': False,
    'fico': 719,
    'debt_ratio': 31.7,
    'consumer_bmi': 27.9}

Consumer Code Example pdhico.calculate_consumer_risk(**example_consumer_data) = 0.63

FIGURE 12

PDHICO Score = (1 - P(loss) * 100)

PDHICO Score = ((1 − 0.37) * 100) = 63

| PDHICO Score Range | PDHICO Score Category |
|---|---|
| 94-100 | A |
| 90-93 | A- |
| 87-89 | B+ |
| 83-86 | B |
| 80-82 | B- |
| 77-79 | C+ |
| 73-76 | C |
| 70-72 | C- |
| 67-69 | D+ |
| 63-66 | D |
| 60-63 | D- |
| < 60 | F |

PDHCO Example Category = 'D'

HEALTH LENDING SYSTEM AND METHOD USING PROBABILISTIC GRAPH MODELS

PRIORITY CLAIM/RELATED APPLICATION

This application claims the benefit under 35 USC 119(e) and priority under 35 USC 120 to U.S. Provisional Patent Application Ser. No. 62/105,503, filed on Jan. 20, 2015, and entitled "Health Lending System and Method Using Probabilistic Graph Models", the entirety of which is incorporated herein by reference.

FIELD

The disclosure relates generally to a health system and method and in particular to a health lending system and method.

BACKGROUND

The problem of financial credit scoring is a very challenging and important financial analysis problem. The main challenge with the credit risk modeling and assessment is that the current models are riddled with uncertainty. The estimation of the probability of default (insolvency), modeling correlation structure for a group of connected borrowers and estimation of amount of correlation are the most important sources of uncertainty that can severely impair the quality of credit risk models.

Many techniques have already been proposed to tackle this problem, ranging from statistical classifiers to decision trees, nearest-neighbor methods and neural networks. Although the latter are powerful pattern recognition techniques, their use for practical problem solving (and credit scoring) is rather limited due to their intrinsic opaque, black box nature. The best known method in the industry is the Fair Isaac Corporation (FICO®) score. The FICO Score® is calculated from several different pieces of credit data in a credit report of a user. The data may be grouped into five categories as shown in FIG. 1. The percentages in the chart in FIG. 1 reflect how important each of the categories is in determining how the FICO score of each user is calculated.

The FICO Score considers both positive and negative information in a credit report. For example, late payments will lower your FICO Score, but establishing or re-establishing a good track record of making payments on time will raise your score. There are several credit reporting companies that work in conjunction with each other, such as Equifax and Transunion to name but a few organizations. However these companies are not able to properly align themselves to a risk management model that matches health based loans. Specifically they do not know the demographics, the place of living, the occupation, the length of employment and dependents of the person. Further in the case of health based services and loans, the risk are increased due to the unhealthy nature of the consumer who is getting the health service and must pay back the loan.

The recent upsurge in health care costs has seen an increased interest in lending to consumers for health services. It is desirable to provide a system and method for determining a health credit score that models the risk of a health care loan to a consumer.

BRIEF DESCRIPTION OF THE DRAWINGS

FIG. 9 illustrates an example of a PDHICO Provider/Payer example input data for the risk assessment;
FIG. 11 illustrates an example of the output of the system for the PDHICO Provider/Payer example data in FIG. 9;
FIG. 12 illustrates an example of a PDHICO Consumer example input data for the risk assessment;
FIG. 14 illustrates an example of the output of the system for the PDHICO consumer example data in FIG. 12.

DETAILED DESCRIPTION OF ONE OR MORE EMBODIMENTS

The disclosure is particularly applicable to a cloud based system and method for health lending using a health credit ("HICO") score that may be generated from a probabilistic graph model and it is in this context that the disclosure will be described. It will be appreciated, however, that the system and method has greater utility since it may use other models in order to generate the HICO and may be implemented in different manners that those described below that would be within the scope of the disclosure. Although the health lending system is shown integrated with a health services system in the figures and descriptions below, the health lending system also may be a standalone system or integrated into other systems.

The health credit score ("HICO") generated by the system and method described below has several factors that differentiate the HICO from the credit score described above. The HICO is a score that is a risk measure placed on all entities of a healthcare transaction in which a company that owns or operates the system may have an interest or a company that utilizes the HICO score for its risk assessment. Each entity may be a health service consumer, a health service provider or a health service payer. However, the system and method described herein may be used to perform a risk measure on various other entities that are part of the health services industry or space. For purposes of illustration below, the description below may consider the entity types described above and then consider the specific risk each entity poses as well as the data and models that may be used to generate the HICO.

Figure 1:
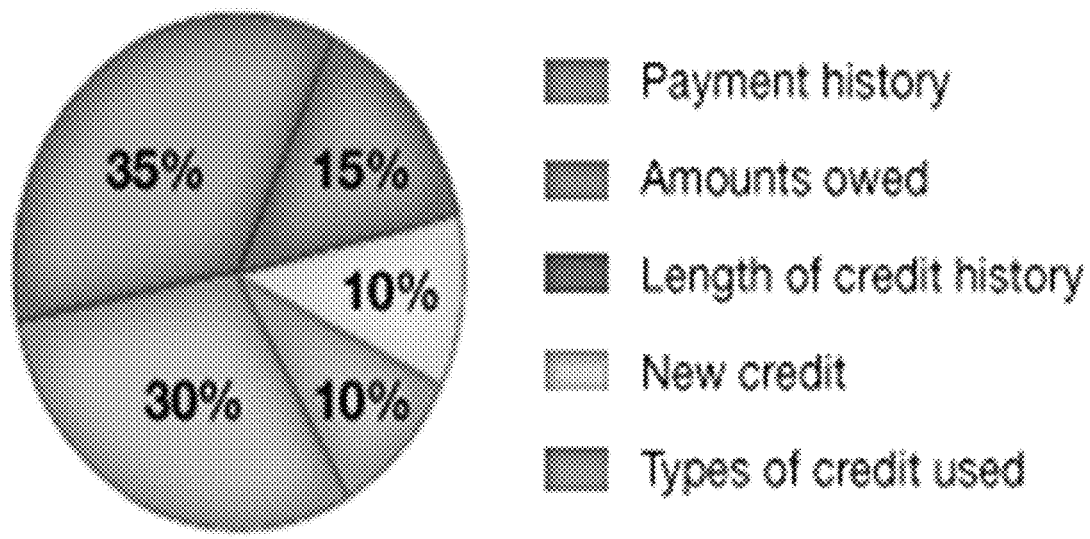
FIG. 1 illustrates an example of a known FICO score.
Figure 2:
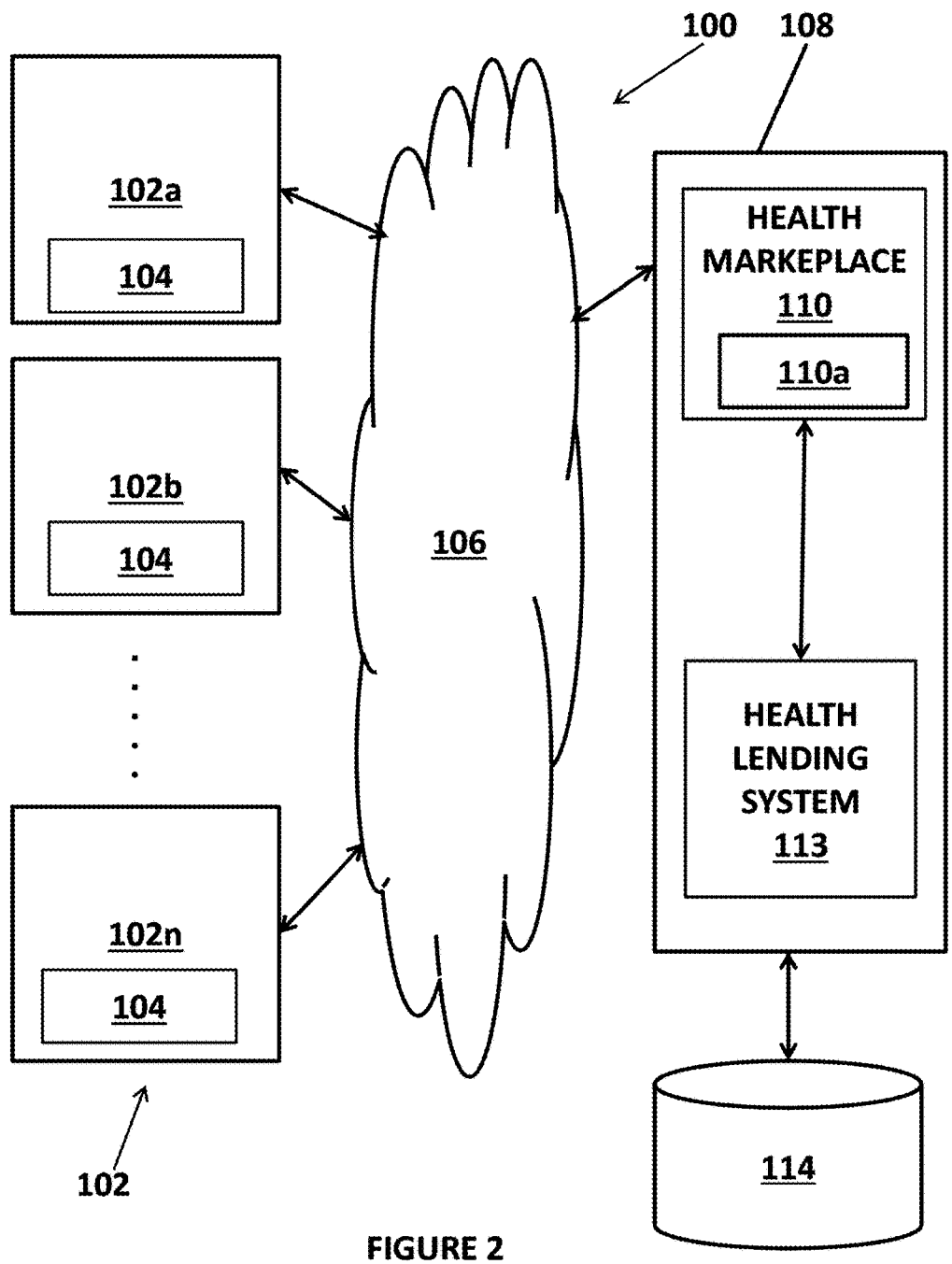
FIG. 2 illustrates a health services system that may incorporate a health lending system.

FIG. 2 illustrates a health services system 100 that may incorporate a health lending system. The health services system 100 may have one or more computing devices 102 that connect over a communication path 106 to a backend system 108. Each computing device 102, such as computing devices 102a, 102b, 102n as shown in FIG. 1, may be a processor based device with memory, persistent storage, wired or wireless communication circuits and a display that allows each computing device to connect to and couple over the communication path 106 to a backend system 108. For example, each computing device may be a smartphone device, such as an Apple Computer product, Android OS based product, etc., a tablet computer, a personal computer, a terminal device, a laptop computer and the like. In one embodiment shown in FIG. 2, each computing device 102 may store an application 104 in memory and then execute that application using the processor of the computing device to interface with the backend system. For example, the application may be a typical browser application or may be a mobile application. The communication path 106 may be a wired or wireless communication path that uses a secure protocol or an unsecure protocol. For example, the communication path 106 may be the Internet, Ethernet, a wireless data network, a cellular digital data network, a WiFi network and the like.

The backend system 108 may have a health marketplace engine 110 and a health lending system 113 that may be coupled together. Each of these components of the backend system may be implemented using one or more computing resources, such as one or more server computers, one or more cloud computing resources and the like. In one embodiment, the health marketplace engine 110 and the health lending system 113 may each be implemented in software in which each has a plurality of lines of computer code that are executed by a processor of the one or more computing resources of the backend system. Thus, in that embodiment, the processor of the one or more computing resources of the backend system is configured to perform the operations and functions of the marketplace and health lending system as described below. In other embodiments, each of the health marketplace engine 110 and the health lending system 113 may be implemented in hardware such as a programmed logic device, a programmed processor or microcontroller and the like. The backend system 108 may be coupled to a store 114 that stores the various data and software modules that make up the healthcare system and the health lending system. The store 114 may be implemented as a hardware database system, a software database system or any other storage system.

The health marketplace engine 110 may allow practitioners that have joined the healthcare social community to reach potential clients in ways unimaginable even a few years ago. In addition to giving practitioners a social portal with which to communicate and market themselves with consumers, the marketplace gives each healthcare practitioner the ability to offer their services in an environment that is familiar to users of Groupon, Living Social, or other social marketplaces.

The health lending system, as described below, is a system that receives data about an entity involved in a health services transaction and then generates a risk measure for the entity involved in the health services transaction. In one embodiment, the risk measure may be in the form of a health credit score ("HICO") that is a risk measure placed on all entities of a healthcare or health services transaction for a company that owns or operates the system may have an interest or a company that utilizes the HICO score for its risk assessment. Each entity may be a health service consumer, a health service provider or a health service payer. However, the system and method described herein may be used to perform a risk measure on various other entities that are part of the health services industry or space. In one embodiment, the risk measure may be based on a probabilistic graph model as described below.

Figure 3:
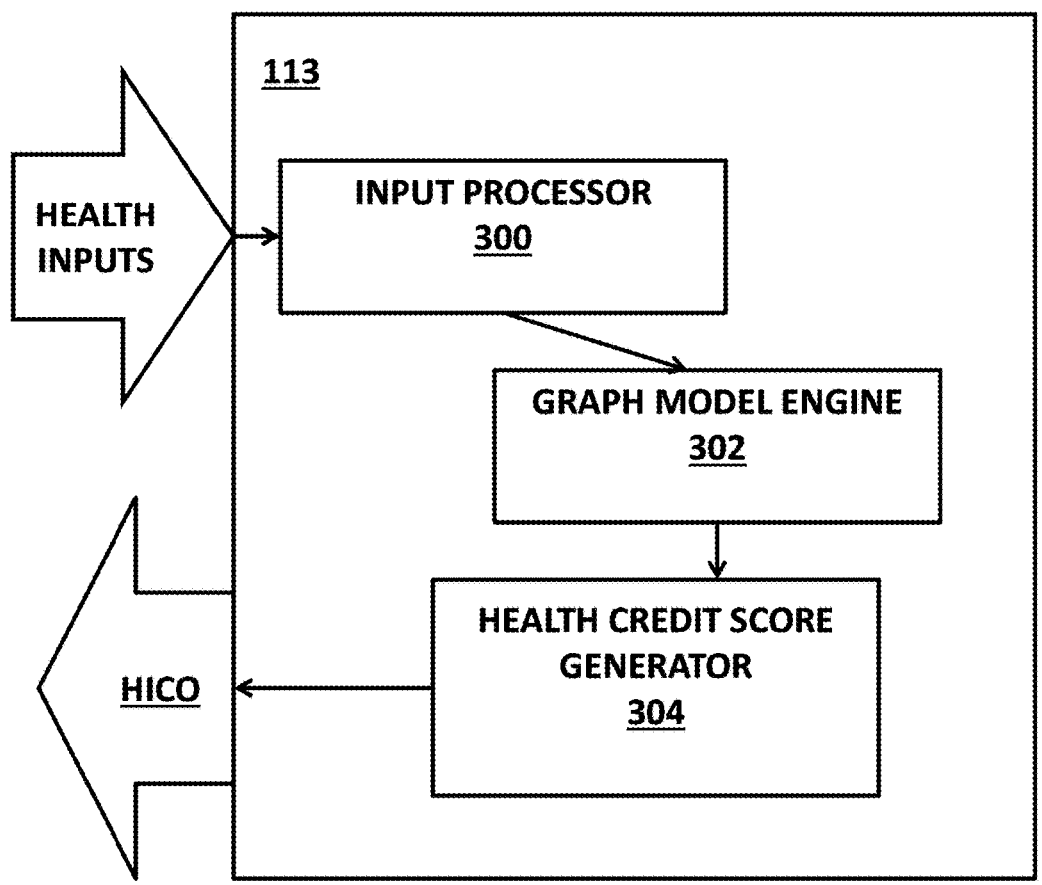
FIG. 3 illustrates more details of the health lending system.

FIG. 3 illustrates more details of the health lending system 113. The health lending system 113 may have an input processor 300 that receives health data input information about an entity and processes it for use by the health lending system 113 such as by, for example, performing an ETL process. The output from the input processor may be fed into a graph model engine 302 that generates a probabilistic graph model based on the health data information for the entity and the output from the graph model engine 302 may be fed into a health credit score generator 304 that generates a health credit score for the entity based on the probabilistic graph model.

Now, the health data input information for the health lending system is described in more detail. The health data input information may include one or more vectors of data that may be generated by an "Extract Transform and Load Process (ETL)" and accessible via the health system using Application Programmer Interfaces (APIs). An example of the data entities that may be used for the Probabilistic Graph structure(s) and the graph model engine 302 appear below. However, additional or other data vectors may be used and those other data vectors may be from other ETL processes. Thus, the example data vectors below are merely illustrative and the disclosure is directed to various different types of data vectors that may be used by the graph model engine.

Consumer Entity

In some embodiments, the health services system may be a hybrid bank/insurer in which the consumers present two possible risk profiles. Specifically, the health services system may provide consumers with traditional health insurance as well as lend them money to pay for health services.

Health Services Lending

In the context of lending money for health services (including health care procedures), the main risk is that the consumer defaults on the loan, thus the main metrics for determining default risk will probably be measures like the known FICO credit score, credit history, available assets (liquid and non-liquid), willingness and/or ability to back the loan by collateral, etc. The overall current FICO model for creditworthiness breaks down as follows:

35% Payment History
    30% Debt Burden
    15% Length of credit history
    10% Types of credit used
    10% Recent searches for credit
    Health Insurance The setting of risk adjustment in terms of health insurance premiums is an extremely complicated and regulated (especially under the ACA) process. The system may also collect data on plan members that may not be a part of the usual risk models in exchange for lower premiums. These datasets could possibly include data from personal wearable devices (Fitbit, Jawbone, smartphone apps) that track lifestyle and biological measurements, as well as past medical records.

For health insurance lending, the health system may have the following information about each person who wants health insurance.

Basic demographics (i.e. location, gender, DOB)
    Insurance Information
    Member ID
    Group ID
    Total deductible
    Remaining deductible
    Dependents
    Marketplace Interactions
    Specialties Searched
    Conditions Searched Purchases made
Log in frequency
Providers rated/reviewed
Self Reported Health Statistics Via Wearable APIs
BMI
Smoker status
Activity Level
Wellness program memberships
Financial Information
FICO Credit Score
Credit reports
Assets/Debts
Lending data from Lending Club
Social Network Interaction Data
twitter, facebook, linked
Wearable API Data
Measured activity level
Sleep cycles
Provider Entities In addition to processing insurance claims for providers, the health lending system may also immediately pay providers for their services instead of them having to wait for the payer to process a claim and then the health lending system is reimbursed from the payer. The risk in immediately paying providers for services rendered is that either the price we pay the provider is more than the price that will be reimbursed by the payer or worse that the service is not covered at all by the consumer's insurance. An analysis of current trends shows that on average for both private insurance and Medicare, providers submit claims for higher than the allowed price with the mentality for providers to bill at the highest price and hope for the best. The application of the current system accurately predicts what a payer is actually going to pay for a given claim so that we can minimize the number of transactions where the amount we pay the provider is higher than the amount reimbursed by the payer.

The health lending system has various information about each provider including:
Provider Demographics (Age, Gender, Location)
Medical Education
Where and when they went to medical school
Where and when they did their residencies/fellowships
Specialties
Credentials
Hospital affiliations
Pricing
Submitted and paid prices from medicare
Cash prices
Services listed on the marketplace
Responses to requests for quote
Ratings, Reviews, Recognitions
Reviews and ratings from marketplace
Malpractice Sanctions from state licensure bodies we receive from the American Medical Association
Ratings and Reviews
Claims Statistics
Number of claims submitted, submitted price, reimbursed price per procedure
Number of rejected claims per procedure
Payer Entities (Aka Insurance Carriers, Trading Partners)

In the situation where the health lending system immediately remit payment to a provider for a service, the health lending system then submits the claim to the payer to collect payment. Like with the providers, the main risk is in the amount reimbursed from the payer for a service and the length of time it takes for the reimbursement.

The health lending system has various information about each payer including (from the processing of X12 transactions):
Payment Statistics: How much does payer X pay on average for procedure Y.
Statistics about time taken to process claims (i.e. average processing time, average time per procedure, etc.)
Statistics about rejected claims. Analysis of claims in general and claims segmented by payer will probably allow us to build predictive models for determining the probability that a claim will be rejected.

Thus, for each of the above entities, the health lending system may assess or predict the risk associated with the transaction with each of the above entities. The risk prediction may be a mixture of the three scores based on a probability model.

Figure 4:
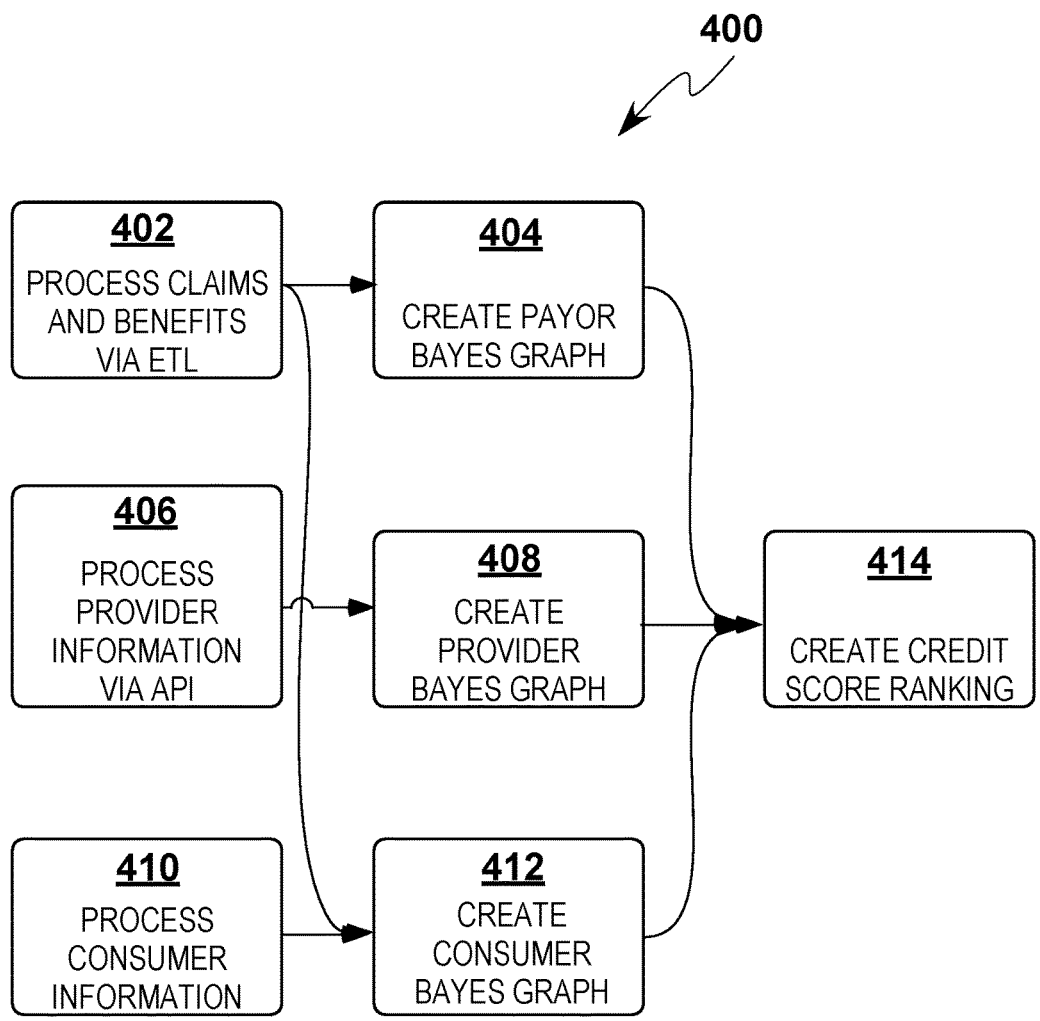
FIG. 4 illustrates a method for predicting risk.

FIG. 4 illustrates a method 400 for predicting risk for each of the different entities that may be performed, in one embodiment, by the health lending system 113 shown in FIGS. 2-3. The method illustrated in FIG. 4 also may be performed by software that is a plurality of lines of computer code that may be executed by a processor of the one or more computing resources so that the processor is configured to perform the operations and functions of the risk prediction as described below. In other embodiments, the method may be performed using hardware such as a programmed logic device, a programmed processor, a microcontroller, an application specific integrated circuit and the like.

As shown in FIG. 4, the method may receive, for a payor, information for the risk prediction based on processing claims and benefits (examples of which are set forth above) via ETL (402). When the health lending component 113 in FIG. 3 is performing the method, the input processor 300 may perform this processing. The information about the payor may be used in the method to create a payor Bayes graph (404). When the health lending component 113 in FIG. 3 is performing the method, the graph model engine 302 may create this Bayes graph. The Bayes graph for the payor may also exchange data with a generated provider Bayes graph.

For a provider entity, the method may process provider information (examples of which are set forth above) via an API (406). When the health lending component 113 in FIG. 3 is performing the method, the input processor 300 may perform this processing. The information about the provider may be used in the method to create a provider Bayes graph (408). When the health lending component 113 in FIG. 3 is performing the method, the graph model engine 302 may create this Bayes graph. The provider Bayes graph may also exchange data with the payer Bayes Graph.

For a consumer entity, the method may process consumer information (examples of which are set forth above) (410). When the health lending component 113 in FIG. 3 is performing the method, the input processor 300 may perform this processing. The information about the consumer (and the claims and benefits information from the ETL) may be used in the method to create a consumer Bayes graph (412). When the health lending component 113 in FIG. 3 is performing the method, the graph model engine 302 may create this Bayes graph.

As shown, one or more of the created Bayes graphs may be used in the method to create a health credit risk score ranking (414). When the health lending component 113 in FIG. 3 is performing the method, the health credit score generator 304 may generate the score(s). An example of this method is described below starting at FIG. 9. Thus, the method generates one or more health credit risk score(s) that may be used by the health lending system to assess the risk of the health services related lending described above.

In the above method, a Bayesian network classifiers is used that provides the capacity of giving a clear insight into the structural relationships in the domain under investigation. In addition, as of late, Bayesian network classifiers have had success for financial credit scoring. In the method, a BeliefNetwork or a network of Bayes Nets which is also called a Probabilistic Graph Model (PGM) may be used.

The method uses probabilistic graphs for modeling and assessment of credit concentration risk based on health and medical behaviors as a function of the risk. The destructive power of credit concentrations essentially depends on the amount of correlation among borrowers. However, borrower company's correlation and concentration of credit risk exposures have been difficult for the banking industry to measure in an objective way as they are riddled with uncertainty. As a result, banks do not manage to make a quantitative link to the correlation driving risks and fail to prevent concentrations from accumulating. However, since the health lending system and method has the ability to exact health and medical behaviors tied to the consumer, the method creates BeliefNetworks that provide an attractive solution to the usual credit scoring problems, specifically within the health domain to show how to apply them in representing, quantifying and managing the uncertain knowledge in concentration of "health credits risk exposures".

The method may use a stepwise Belief network model building scheme and the method may incorporate prior beliefs regarding the risk exposure of a group of related behavior such as office revisits and outcomes and then update these beliefs through the whole model with the new information as it is learned. The method may use a specific graph structure, BeliefNetwork network, and the model provides better understanding of the concentration risk accumulating due to strong direct or indirect business links between borrowers and lenders as a function of the health data that is used. The method also may use three model BeliefNetworks and the mutual information and construct a BeliefNetwork that is a reliable model that can be implemented to identify and control threat from concentration of credit exposures.

A Bayesian network (BN) represents a joint probability distribution over a set of discrete attributes. It is to be considered as a probabilistic white-box model consisting of a qualitative part specifying the conditional (inter)dependencies between the attributes and a quantitative part specifying the conditional probabilities of the data set attributes. Formally, a Bayesian network consists of two parts, B=<G, θ>, wherein a directed acyclic graph G consisting of nodes and arcs and one or more conditional probability tables θ=(θx1, . . . θxn). The nodes are the attribute $X_1 \ldots X_n$ whereas the arcs indicate direct dependencies. The Bayesian network is essentially a statistical model that makes it feasible to compute the (joint) posterior probability distribution of any subset of unobserved stochastic variables, given that the variables in the complementary subset are observed.

The graph G then encodes the independence relationships of the domain. The network B represents the following joint probability distribution:

$$P_B(X_1 \ldots X_n) = \Pi_{i=1}^{n} Pb(Xi|\Pi Xi) = \Pi_{i=1}^{n} \theta Xi|\Pi Xi \quad \text{(Equation 1)}$$

This yields a Bayesian probabilistic graph structure that is familiar to those trained in the art.

Given this basic functionality, a baseline for discreet tractable variables is created where inference is exact. In our cases of the three probabilistic graph models (as shown in FIG. 4), we have three tractable inference models.

In order to improve the performance of the models and graphs, for continuous variables such as pricing information, the method may utilize Markov chain Monte Carlo (MCMC hereafter) which samples directly from the posterior distributions. The method may also use the well known Metropolis-Hastings algorithm for Markov Chains. The Metropolis-Hastings algorithm was first adapted for structural learning of Bayesian and Markov Networks by Madigan and York. In the method; metropolis—Hastings and other MCMC algorithms are generally used for sampling from multi-dimensional distributions, especially when the number of dimensions is high. In our case of the Health Credit Score Models described above, the models are considered high dimensionality.

The BeliefNetworks building process for the provider network model and build process may use the following code example:

```
provider_bayes_net =
build_bayes_belief_net
twork(
    prob_procedures_performed_by_specialty_count,
    prob_procedures_performed_count,
    prob_provider_procedure_experience,
    prob_provider_age,
    prob_provider_experience,
    prob_provider_revoked_license,
    prob_provider_ability,
    prob_claim_line_edited_to_zero,
    prob_good_payer_price_data,
    prob_pd_payment_payer_paid_difference,
    prob_loss,
    domains=dict(
    procedures_performed_by_specialty_count=variable_range_bins,
    procedures_performed_count=variable_range_bins,
    provider_procedure_experience=variable_range_bins,
    provider_age=['veryold', 'old', 'middle_age', 'young'],
    provider_experience=variable_range_bins,
    provider_revoked_license=boolean_variable_vals,
    provider_ability=variable_range_bins,
    claim_line_edited_to_zero=boolean_variable_vals,
    good_payer_price_data=boolean_variable_vals,
        pd_payment_payer_paid_difference=variable_range_bins,
    loss=boolean_variable_vals
    ))
    return provider_bayes_net
```

Figure 5:
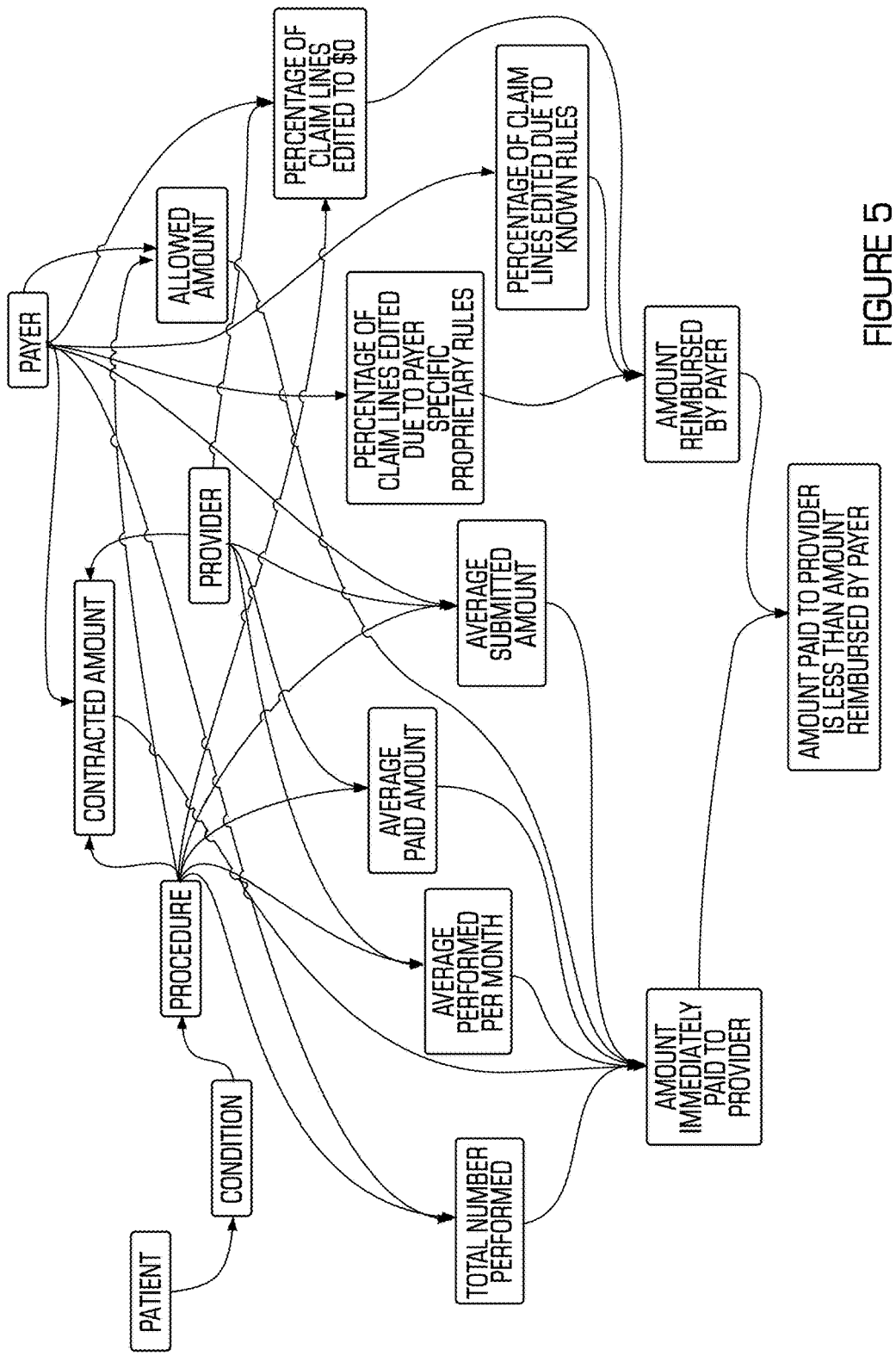
FIG. 5 illustrates an example of a provider Bayes risk network.
Figure 6:
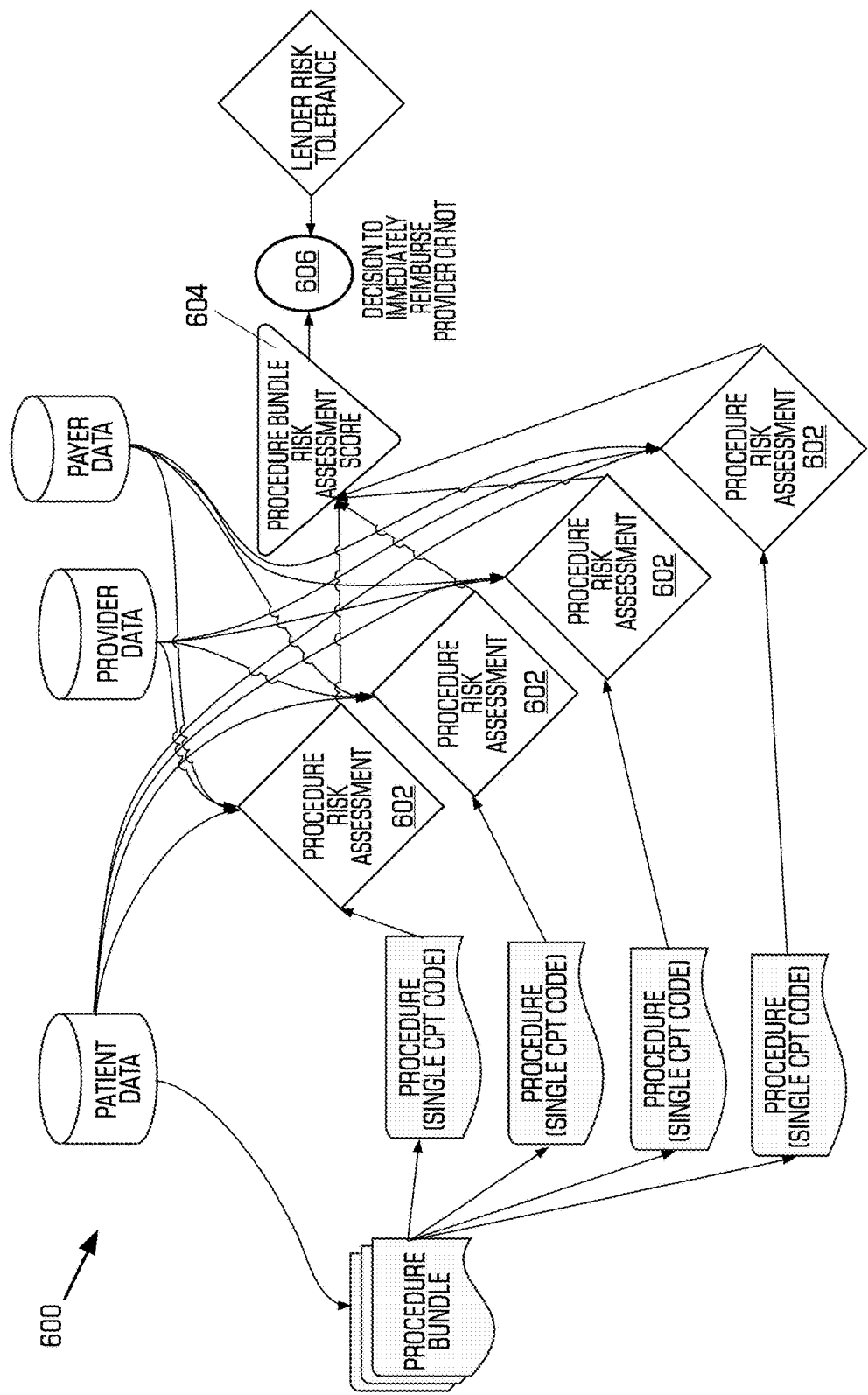
FIG. 6 illustrates an example of a method for a provider Bayes model generation.

An example of the provider payer risk Bayes network in shown in FIG. 5. As shown in FIG. 5, the various information for a provider risk assessment are shown. FIG. 6 shows an example of a method 600 for a provider Bayes model generation starting with a procedure bundle for each health procedure wherein each procedure may be a single CPT code. A typical medical/health procedure usually consists of more than one billing procedure code (CPT code). The method calculates a PDHICO score for each line item (CPT code) and then combines them into an overall procedure bundle score. The method may use the patient data, payer data and/or provider data to generate a procedure risk assessment 602 for each of the procedures. Based on the risk assessment of each of the procedures, the method may determine a procedure bundle risk assessment score 604. Based on the procedure bundle risk assessment score, the health lending system may determine (606) whether or not to immediately reimburse the provider that may depend in part on a lender risk toleration.

Figure 7:
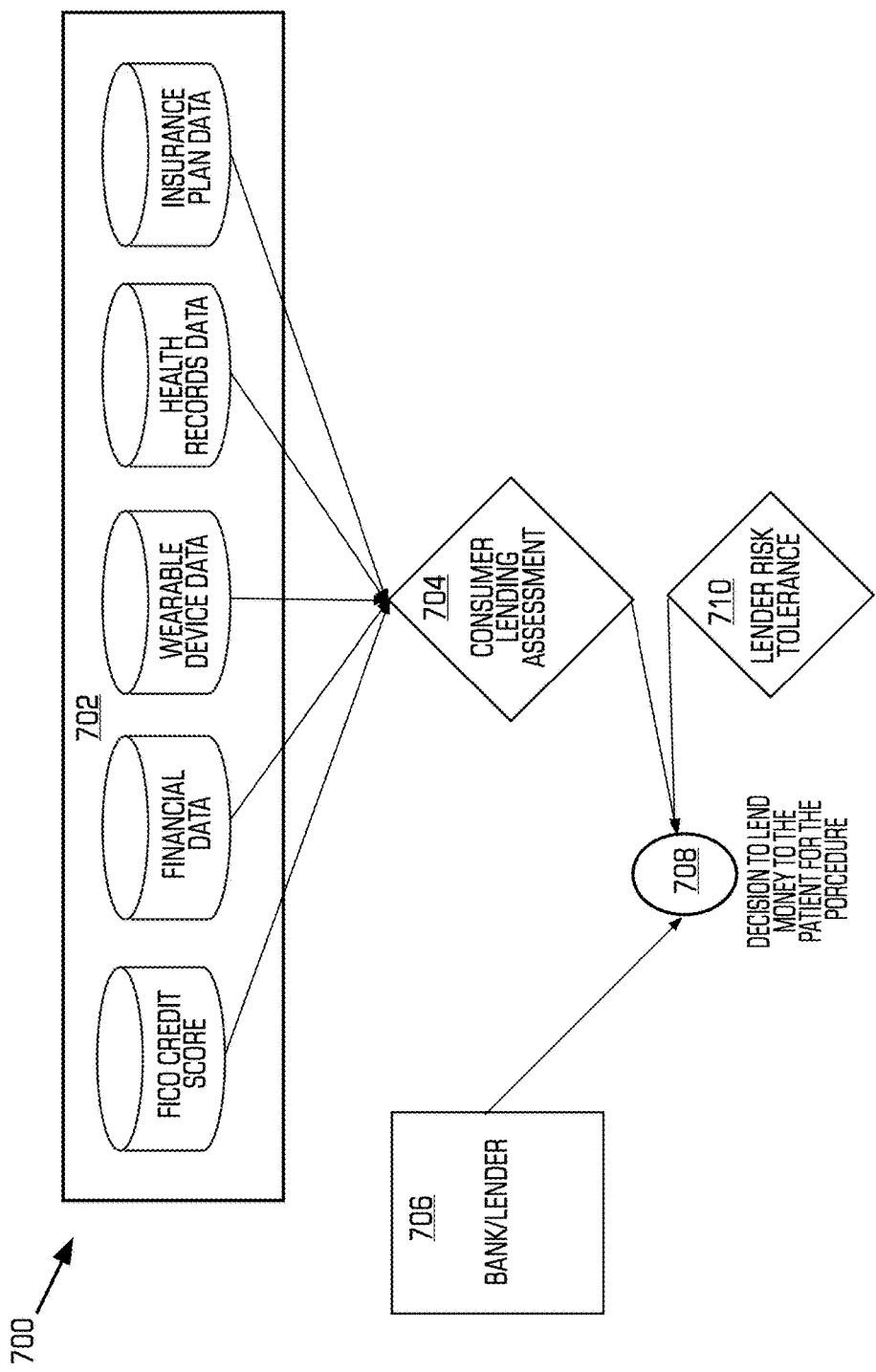
FIG. 7 illustrates an example of a method for consumer risk modeling.

FIG. 7 illustrates an example of a method 700 for consumer risk modeling in which information about the consumer (702) is used. When the health lending component 113 in FIG. 3 is performing the method, the graph model engine 302 may perform the method. The information about the consumer may include a FICO credit score, financial data, wearable device data, health record data and insurance plan data. The information about the consumer may be used to make a consumer lending assessment (704). The consumer lending assessment 704 may be combined with data about a bank/lender (706) to determine (708) whether to lend money to the patient for the procedure. The determination about lending the money may also depend on the lender risk tolerance (710).

Figure 8:
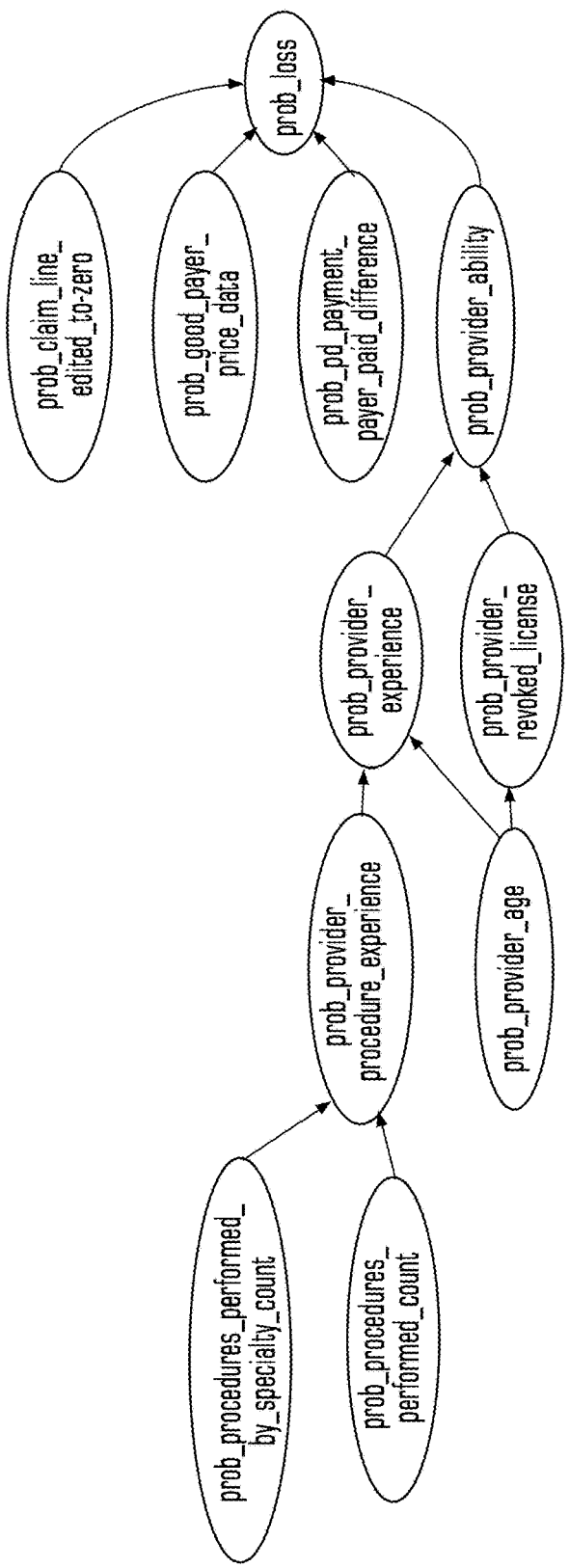
FIG. 8 illustrates an example of the output of the Belief-Network graph inference model.

FIG. 8 illustrates an example of the output of the Belief-Network graph inference model that shows the calculated probabilities that ultimately result in a probability of loss if the lending is made to a particular consumer.

Figure 10:
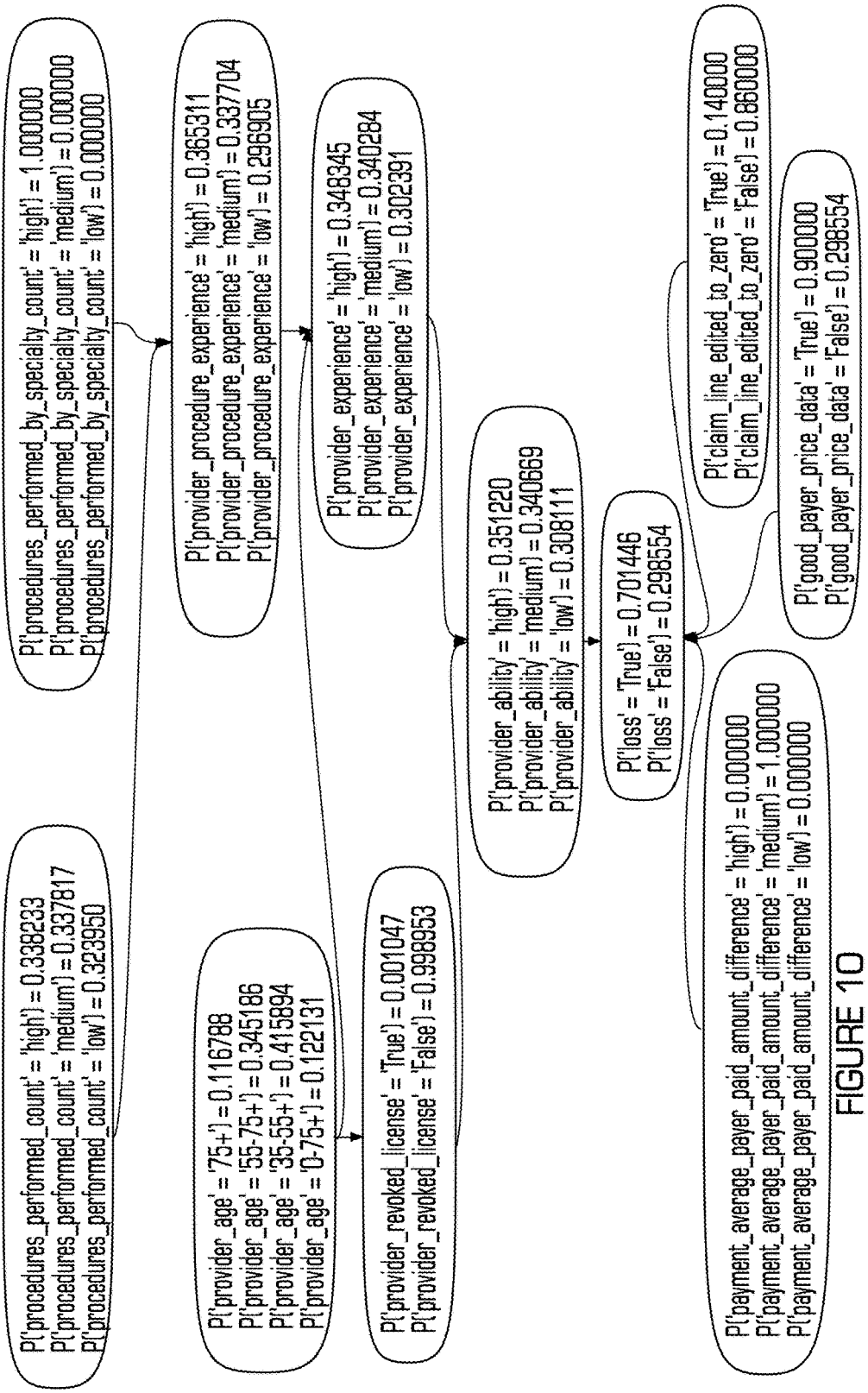
FIG. 10 illustrates an example of a risk graph for the PDHICO Provider/Payer example data in FIG. 9.

FIG. 9 illustrates an example of a PDHICO Provider/Payer example input data for the risk assessment. Thus, FIG. 9 shows exemplary input data including a reimbursed price, reimbursed price stats and procedures performed by the provider. FIG. 10 illustrates an example of a risk graph for the PDHICO Provider/Payer example data in FIG. 9 generated by the system and method described above. As shown in FIG. 10, various values for the example data in FIG. 9 are generated and placed into the risk graph. For example, the probability of loss, P(loss), is calculated as 0.701 as shown in FIG. 10. The probability of loss may be calculated using the methodology described above and using equation (1). The method may use the probabilities encoded in the graphical model to calculate the conditional probability P(loss=True|procedures_performed_by_specialty_count= "high", payment_average_payer_paid_amount_difference="medium"). This is where the representational efficiency of the graphical model comes into play as the conditional probability table for the resulting equation has more than 177, 147 terms. FIG. 11 illustrates an example of the output of the system for the PDHICO Provider/Payer example data in FIG. 9 including the scores generated by the system. In one embodiment, the risk score may be calculated as (1−P(loss)*100). Then, from the example data in FIG. 9, the system generates a risk score of 30 calculated as (1−0.7)*100) from the value calculated in FIG. 9.

Figure 13A:
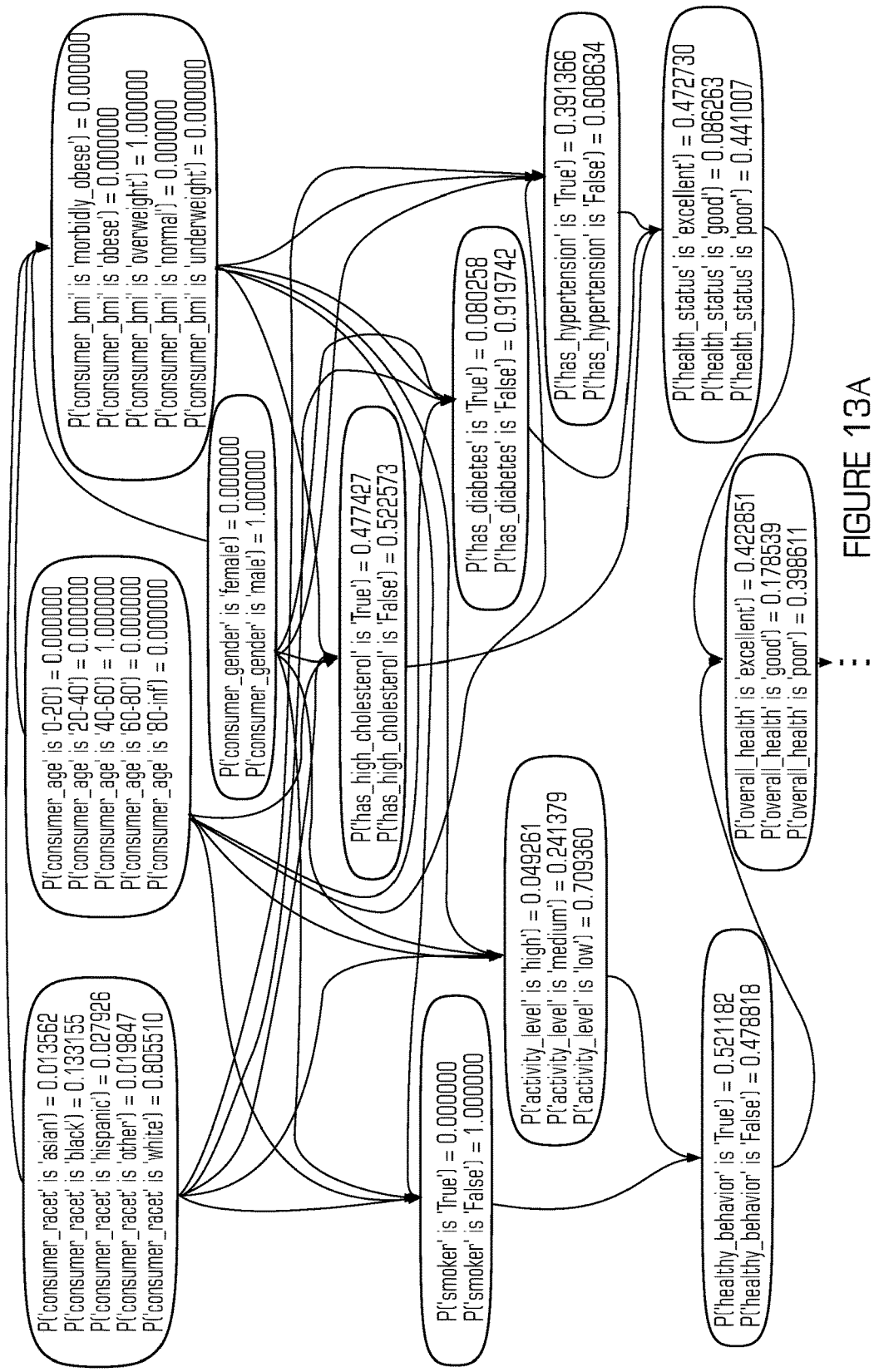
FIG. 13A and FIG. 13B illustrate an example of a risk graph for the PDHICO consumer example data in FIG. 12.
Figure 13B:
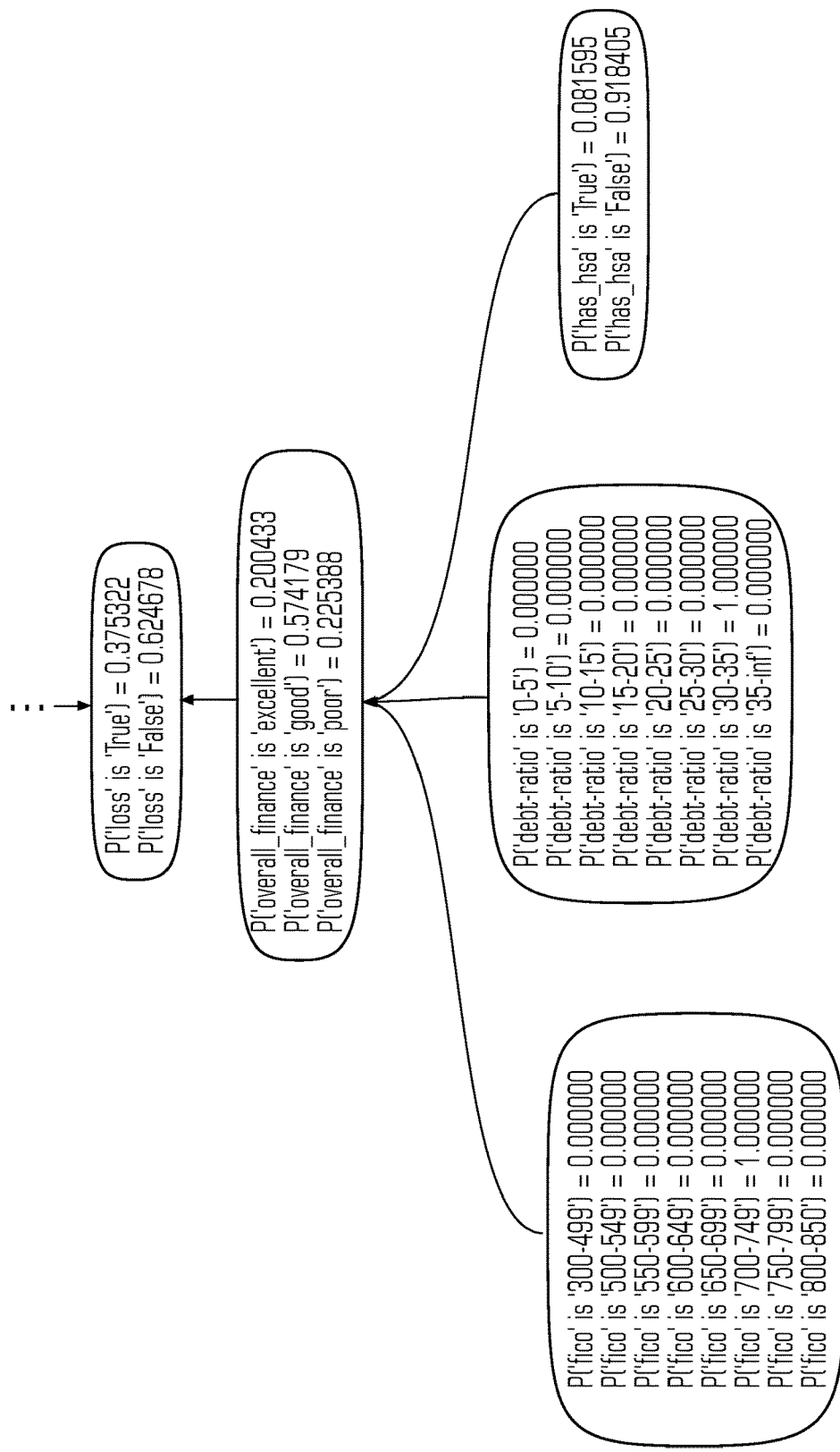

FIG. 12 illustrates an example of a PDHICO Consumer example input data for the risk assessment in which various particulars about the consumer including health details and financial details are stored. In one embodiment, the consumer risk may be calculated as 0.63 based on the consumer input data. FIG. 13A and FIG. 13B illustrate an example of a risk graph for the PDHICO consumer example data in FIG. 12 generated by the system and method described above. As shown in FIG. 13A and FIG. 13B, various values for the example data in FIG. 12 are generated and placed into the risk graph. For example, the probability of loss, P(loss), is calculated as 0.37 as shown in FIG. 13A and FIG. 13B. The probability of loss may be calculated using the methodology described above and using equation (1). The method may use the probabilities encoded in the graphical model to calculate the conditional probability P(loss=True|onsumer_bmi="overweight", consumer_gender="male", smoker="false", consumer_age="40-69", debt_ratio="30-35", fico="700-749") This is where the representational efficiency of the graphical model comes into play as the conditional probability table for the resulting equation has more than 43,046,721 terms. FIG. 14 illustrates an example of the output of the system for the PDHICO consumer example data in FIG. 12 including the scores generated by the system. In one embodiment, the risk score may be calculated as (1−P(loss)*100). Then, from the example data in FIG. 12, the system generates a risk score of 63 calculated as (1−0.37)*100) from the value calculated in FIG. 12.

The foregoing description, for purpose of explanation, has been described with reference to specific embodiments. However, the illustrative discussions above are not intended to be exhaustive or to limit the disclosure to the precise forms disclosed. Many modifications and variations are possible in view of the above teachings. The embodiments were chosen and described in order to best explain the principles of the disclosure and its practical applications, to thereby enable others skilled in the art to best utilize the disclosure and various embodiments with various modifications as are suited to the particular use contemplated.

The system and method disclosed herein may be implemented via one or more components, systems, servers, appliances, other subcomponents, or distributed between such elements. When implemented as a system, such systems may include an/or involve, inter alia, components such as software modules, general-purpose CPU, RAM, etc. found in general-purpose computers. In implementations where the innovations reside on a server, such a server may include or involve components such as CPU, RAM, etc., such as those found in general-purpose computers.

Additionally, the system and method herein may be achieved via implementations with disparate or entirely different software, hardware and/or firmware components, beyond that set forth above. With regard to such other components (e.g., software, processing components, etc.) and/or computer-readable media associated with or embodying the present inventions, for example, aspects of the innovations herein may be implemented consistent with numerous general purpose or special purpose computing systems or configurations. Various exemplary computing systems, environments, and/or configurations that may be suitable for use with the innovations herein may include, but are not limited to: software or other components within or embodied on personal computers, servers or server computing devices such as routing/connectivity components, handheld or laptop devices, multiprocessor systems, microprocessor-based systems, set top boxes, consumer electronic devices, network PCs, other existing computer platforms, distributed computing environments that include one or more of the above systems or devices, etc.

In some instances, aspects of the system and method may be achieved via or performed by logic and/or logic instructions including program modules, executed in association with such components or circuitry, for example. In general, program modules may include routines, programs, objects, components, data structures, etc. that perform particular tasks or implement particular instructions herein. The inventions may also be practiced in the context of distributed software, computer, or circuit settings where circuitry is connected via communication buses, circuitry or links. In distributed settings, control/instructions may occur from both local and remote computer storage media including memory storage devices.

The software, circuitry and components herein may also include and/or utilize one or more type of computer readable media. Computer readable media can be any available media that is resident on, associable with, or can be accessed by such circuits and/or computing components. By way of example, and not limitation, computer readable media may comprise computer storage media and communication media. Computer storage media includes volatile and non-volatile, removable and non-removable media implemented in any method or technology for storage of information such as computer readable instructions, data structures, program modules or other data. Computer storage media includes, but is not limited to, RAM, ROM, EEPROM, flash memory or other memory technology, CD-ROM, digital versatile disks (DVD) or other optical storage, magnetic tape, magnetic disk storage or other magnetic storage devices, or any other medium which can be used to store the desired information and can accessed by computing component. Communication media may comprise computer readable instructions, data structures, program modules and/or other components. Further, communication media may include wired media such as a wired network or direct-wired connection, however no media of any such type herein includes transitory media. Combinations of the any of the above are also included within the scope of computer readable media.

In the present description, the terms component, module, device, etc. may refer to any type of logical or functional software elements, circuits, blocks and/or processes that may be implemented in a variety of ways. For example, the functions of various circuits and/or blocks can be combined with one another into any other number of modules. Each module may even be implemented as a software program stored on a tangible memory (e.g., random access memory, read only memory, CD-ROM memory, hard disk drive, etc.) to be read by a central processing unit to implement the functions of the innovations herein. Or, the modules can comprise programming instructions transmitted to a general purpose computer or to processing/graphics hardware via a transmission carrier wave. Also, the modules can be implemented as hardware logic circuitry implementing the functions encompassed by the innovations herein. Finally, the modules can be implemented using special purpose instructions (SIMD instructions), field programmable logic arrays or any mix thereof which provides the desired level performance and cost.

As disclosed herein, features consistent with the disclosure may be implemented via computer-hardware, software and/or firmware. For example, the systems and methods disclosed herein may be embodied in various forms including, for example, a data processor, such as a computer that also includes a database, digital electronic circuitry, firmware, software, or in combinations of them. Further, while some of the disclosed implementations describe specific hardware components, systems and methods consistent with the innovations herein may be implemented with any combination of hardware, software and/or firmware. Moreover, the above-noted features and other aspects and principles of the innovations herein may be implemented in various environments. Such environments and related applications may be specially constructed for performing the various routines, processes and/or operations according to the invention or they may include a general-purpose computer or computing platform selectively activated or reconfigured by code to provide the necessary functionality. The processes disclosed herein are not inherently related to any particular computer, network, architecture, environment, or other apparatus, and may be implemented by a suitable combination of hardware, software, and/or firmware. For example, various general-purpose machines may be used with programs written in accordance with teachings of the invention, or it may be more convenient to construct a specialized apparatus or system to perform the required methods and techniques.

Aspects of the method and system described herein, such as the logic, may also be implemented as functionality programmed into any of a variety of circuitry, including programmable logic devices ("PLDs"), such as field programmable gate arrays ("FPGAs"), programmable array logic ("PAL") devices, electrically programmable logic and memory devices and standard cell-based devices, as well as application specific integrated circuits. Some other possibilities for implementing aspects include: memory devices, microcontrollers with memory (such as EEPROM), embedded microprocessors, firmware, software, etc. Furthermore, aspects may be embodied in microprocessors having software-based circuit emulation, discrete logic (sequential and combinatorial), custom devices, fuzzy (neural) logic, quantum devices, and hybrids of any of the above device types. The underlying device technologies may be provided in a variety of component types, e.g., metal-oxide semiconductor field-effect transistor ("MOSFET") technologies like complementary metal-oxide semiconductor ("CMOS"), bipolar technologies like emitter-coupled logic ("ECL"), polymer technologies (e.g., silicon-conjugated polymer and metal-conjugated polymer-metal structures), mixed analog and digital, and so on.

It should also be noted that the various logic and/or functions disclosed herein may be enabled using any number of combinations of hardware, firmware, and/or as data and/or instructions embodied in various machine-readable or computer-readable media, in terms of their behavioral, register transfer, logic component, and/or other characteristics. Computer-readable media in which such formatted data and/or instructions may be embodied include, but are not limited to, non-volatile storage media in various forms (e.g., optical, magnetic or semiconductor storage media) though again does not include transitory media. Unless the context clearly requires otherwise, throughout the description, the words "comprise," "comprising," and the like are to be construed in an inclusive sense as opposed to an exclusive or exhaustive sense; that is to say, in a sense of "including, but not limited to." Words using the singular or plural number also include the plural or singular number respectively. Additionally, the words "herein," "hereunder," "above," "below," and words of similar import refer to this application as a whole and not to any particular portions of this application. When the word "or" is used in reference to a list of two or more items, that word covers all of the following interpretations of the word: any of the items in the list, all of the items in the list and any combination of the items in the list.

Although certain presently preferred implementations of the invention have been specifically described herein, it will be apparent to those skilled in the art to which the invention pertains that variations and modifications of the various implementations shown and described herein may be made without departing from the spirit and scope of the invention. Accordingly, it is intended that the invention be limited only to the extent required by the applicable rules of law.

While the foregoing has been with reference to a particular embodiment of the disclosure, it will be appreciated by those skilled in the art that changes in this embodiment may be made without departing from the principles and spirit of the disclosure, the scope of which is defined by the appended claims.

The invention claimed is:

1. A system, comprising:
a first computer system having a processor and a memory;
a computer system that stores claims and benefits data for a payor;
a computer system that stores provider data for a health care transaction provider;
a computer system that stores consumer data about a consumer of a health care service;

the first computer system hosting an input processor configured to receive data from the computer systems that store claims and benefits data for the payor, provider data and consumer data about a health service transaction and process the data about the health care transaction using an ETL process;

the first computer system hosting a graph model engine that receives the data about the health care transaction and programmatically generates a bayes graph for the payor using the claims and benefits data to generate a payor risk associated with the health care transaction, a bayes graph for the provider using the provider data to generate a provider risk associated with the health care transaction and a bayes graph for the consumer using the consumer data and the claims and benefits data to generate a consumer risk associated with the health care transaction; and the computer system configured to generate a risk measure for the health service transaction using the payor risk, provider risk and consumer risk generated using the bayes graphs for each entity that is part of the health service transaction.

2. The system of 1, wherein the processor is configured to use a probabilistic graph model to generate the risk measure.

3. The system of claim 2, wherein the processor is configured to generate a payor bayes graph, a provider bayes graph and a consumer bayes graph.

4. The system of claim 3, wherein the processor is configured to generate the risk measure by combining the payor bayes graph, the provider bayes graph and the consumer bayes graph.

5. The system of claim 2, wherein the processor is configured to use a stepwise belief network to generate the probabilistic graph model.

6. The system of claim 1, wherein the processor is configured to generate a risk score for an entity involved in the health service transaction.

7. The system of claim 6, wherein the entity is one of a health service consumer, a health service provider and a health service payer.

8. The system of claim 1, wherein the risk measure is a risk score.

9. A method, comprising:

providing a computer system having a processor, memory and a plurality of lines of computer code configured to:

receive and process data about a health service transaction using an ETL process, the data about the health care transaction including claims and benefits data for a payor, provider data for a health care transaction provider and consumer data about a consumer of a health care service;

generate a bayes graph for the payor using the claims and benefits data to generate a payor risk associated with the health care transaction, a bayes graph for the provider using the provider data to generate a provider risk associated with the health care transaction and a bayes graph for the consumer using the consumer data and the claims and benefits data to generate a consumer risk associated with the health service transaction; and generate a risk measure for the health service transaction using the payor risk, provider risk and consumer risk generated using the bayes graphs for each entity that is part of the health service transaction.

10. The method of 9, wherein generating the risk measure further comprises using a probabilistic graph model to generate the risk measure.

11. The method of claim 10, wherein using the probabilistic graph model further comprises generating a payor bayes graph, generating a provider bayes graph and generating a consumer bayes graph.

12. The method of claim 11, wherein generating the risk measure further comprises combining the payor bayes graph, the provider bayes graph and the consumer bayes graph to generate the risk measure.

13. The method of claim 10, wherein using the probabilistic graph model further comprises using a stepwise belief network to generate the probabilistic graph model.

14. The method of claim 9 further comprising generating a risk score for an entity involved in the health service transaction.

15. The method of claim 14, wherein the entity is one of a health service consumer, a health service provider and a health service payer.

16. The method of claim 9, wherein the risk measure is a risk score.

17. An apparatus, comprising:

a processor;

a memory;

the processor configured to receive and process data about a health service transaction using an ETL process, the data about the health care transaction including claims and benefits data for a payor, provider data for a health care transaction provider and consumer data about a consumer of a health care service; and the processor configured to generate a bayes graph for the payor using the claims and benefits data to generate a payor risk associated with the health care transaction, a bayes graph for the provider using the provider data to generate a provider risk associated with the health care transaction and a bayes graph for the consumer using the consumer data and the claims and benefits data to generate a consumer risk associated with the health care transaction and to generate a risk measure for the health service transaction using the payor risk, provider risk and consumer risk generated using the bayes graphs for each entity that is part of the health service transaction.

18. The apparatus of 17, wherein the processor is configured to use a probabilistic graph model to generate the risk measure.

19. The apparatus of claim 18, wherein the processor is configured to generate a payor bayes graph, a provider bayes graph and a consumer bayes graph.

20. The apparatus of claim 19, wherein the processor is configured to generate the risk measure by combining the payor bayes graph, the provider bayes graph and the consumer bayes graph.

21. The apparatus of claim 18, wherein the processor is configured to use a stepwise belief network to generate the probabilistic graph model.

22. The apparatus of claim 17, wherein the processor is configured to generate a risk score for an entity involved in the health service transaction.

23. The apparatus of claim 22, wherein the entity is one of a health service consumer, a health service provider and a health service payer.

24. The apparatus of claim 17, wherein the risk measure is a risk score.

* * * * *